United States Patent
Patag

[11] Patent Number: 6,141,593
[45] Date of Patent: Oct. 31, 2000

[54] CARDIAC LEAD WITH ETEE COATED DBS COIL

[75] Inventor: Alfredo E. Patag, Lake Jackson, Tex.

[73] Assignee: Intermedics Inc., Angleton, Tex.

[21] Appl. No.: 09/189,031

[22] Filed: Nov. 10, 1998

[51] Int. Cl.[7] .................................................. A61N 1/05
[52] U.S. Cl. ......................................................... 607/122
[58] Field of Search ................................... 607/119, 122, 607/115, 116, 123; 600/373–375

[56] References Cited

U.S. PATENT DOCUMENTS

| | | |
|---|---|---|
| 4,938,822 | 7/1990 | Peers-Trevarton . |
| 5,007,435 | 4/1991 | Doan et al. . |
| 5,115,818 | 5/1992 | Holleman et al. . |
| 5,251,643 | 10/1993 | Osypka . |
| 5,257,634 | 11/1993 | Kroll . |
| 5,354,327 | 10/1994 | Smits ...................................... 607/122 |
| 5,476,500 | 12/1995 | Fain et al. . |

FOREIGN PATENT DOCUMENTS

| | | |
|---|---|---|
| 0570710 | 5/1992 | European Pat. Off. . |
| 96/06655 | 8/1994 | WIPO . |

*Primary Examiner*—George R. Evanisko
*Attorney, Agent, or Firm*—Schwegmen, Lundberg, Woessner & Kluth, P.A.

[57] ABSTRACT

A cardiac lead is provided that includes a connector for coupling to a cardiac stimulator and a first flexible insulating sleeve coupled to the connector. A second flexible insulating sleeve is coupled to the connector and has a portion positioned inside the first flexible insulating sleeve. A first conductor wire is provided that has at least a first loop and a second loop. The first and second loops are positioned between the portion of the second flexible insulating sleeve and the first insulating sleeve. A second conductor wire is provided that has a third loop. The third loop is positioned between the portion of the second flexible insulating sleeve and the first insulating sleeve. The first and second conductor wires are spiraled together so that the third loop is positioned between the first and second loops. The lead provides for the union of two conductors in a flexible structure that facilitates passage of a highly curved stylet.

24 Claims, 11 Drawing Sheets

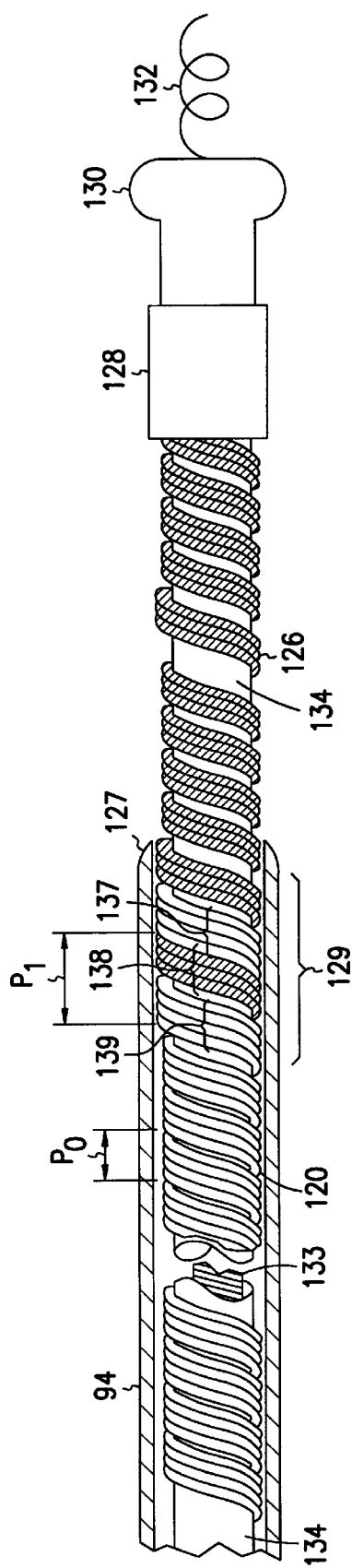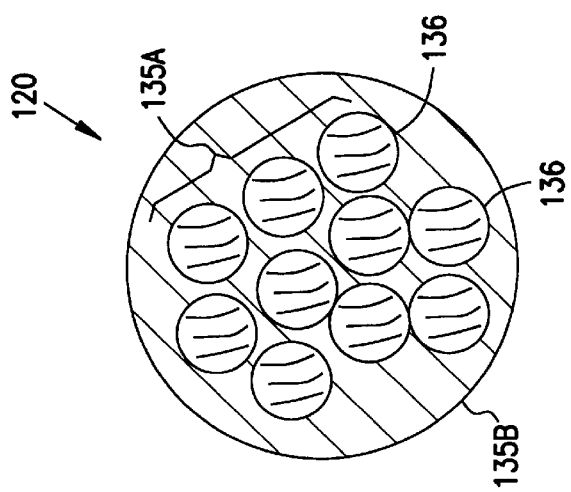
FIG. 8
FIG. 9

CARDIAC LEAD WITH ETEE COATED DBS COIL

BACKGROUND OF THE INVENTION

1. Field of the Invention

This invention relates generally to cardiac stimulator leads, and more particularly to a cardiac stimulator lead having an improved structure for joining the ends of two conductor wires.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices. At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated, flexible, tubular, electrically insulating sleeve that is connected proximally to a connector that is adapted to couple to the header of a cardiac stimulator. In pacing leads, the distal end of the insulating sleeve is joined with a tip electrode. In defibrillator leads, a defibrillator or shock coil commonly projects from the distal end of the insulating sleeve. The shock coil consists of an uninsulated coiled wire wound with a large number of coils. The plurality of coils distribute defibrillation pulses over a much larger surface area of the myocardium than a pacing electrode.

In some conventional defibrillator lead designs, the electrical pathway between the lead connector and the shock coil is provided by a separate conductor wire that is coupled proximally to the connector and secured distally to a crimp assembly. The conventional crimp assembly consists of an inner tubular sleeve over which respective ends of the shock coil and the other conductor wire are positioned and crimped into position by respective outer crimp sleeves. The inner sleeve and the outer sleeves are normally made of titanium or other relatively rigid biocompatible conducting materials. The inner tubular sleeve is of such length that the ends of the shock coil and the other wire are usually not intertwined. The conducting nature of the inner sleeve is relied upon to pass current between the two wires.

A conventional crimp assembly can significantly hamper the movement of a stylet used to spatially manipulate the lead during implantation. For most implantation procedures, the physician inserts a stylet into the lead connector and advances it to the distal tip of the lead. The physician then manipulates the stylet to accurately position the distal end of the lead proximate the endocardial site requiring electrical stimulation. The distal end of the stylet must be inserted through the crimp assembly in order to reach the tip of the lead. This step may not be problematic where the stylet is not bent significantly prior to insertion, as is often the case where the implantation involves a relatively straight pathway through the heart. Fixation to the right ventricular apex is an example of such a relatively straight pathway.

Where the implantation requires the pathway of the lead tip to be deviated, the situation may become more difficult for the physician. For example, fixation to the superior interventricular septum or access to the great cardiac vein via the coronary sinus require the lead tip to be turned abruptly after entry into the heart. This is frequently accomplished by introducing a severe bend in the distal end of the lead, usually after the lead is initially positioned inside the heart. Initially, a straight stylet is used to move the lead into the right atrium. Then the straight stylet is removed and a highly curved stylet is inserted and advanced to the distal end of the lead. The stylet is usually curved by the physician by hand based on the physician's experience and knowledge of the patient's particular anatomy. The radius of curvature of the bend may be quite small.

The initial movement of the highly curved portion of the stylet through the lead may be unremarkable since the majority of the lead is quite flexible. As the curved portion is advanced, the lead is able to temporarily conform to the curvature of the stylet. In contrast to the insulating sleeve, the crimp assembly is quite rigid and cannot conform to the curvature of the stylet. As a result, the physician may encounter significant resistance to further axial movement when the highly curved portion of the stylet encounters the inner sleeve. This undesirable tactile response is more than just a nuisance. The natural tendency of the physician at this point is to apply additional thrust to the proximal end of the stylet to force the curved portion through the inner sleeve. Because the stylet is highly curved and thrust is being applied at the opposite end thereof, the stylet will tend to behave like an unstable column under compression loading. If the rubbing of the inner sleeve is great enough, axial thrust applied by the physician will cause the stylet to buckle and plastically deform at one or more points along its length. With one or more unintended bends in the stylet, the movement of the lead in response to manipulation of the stylet may be unpredictable and the complexity of the implantation procedure increased.

The present invention is directed to overcoming or reducing the effects of one or more of the foregoing disadvantages.

SUMMARY OF THE INVENTION

In accordance with one aspect of the present invention, a cardiac lead is provided that includes a connector for coupling to a cardiac stimulator and a first flexible insulating sleeve coupled to the connector. A second flexible insulating sleeve is coupled to the connector and has a portion positioned inside the first flexible insulating sleeve. A first coiled conductor wire is provided that has at least a first loop and a second loop. The first and second loops are positioned between the second flexible insulating sleeve and the first insulating sleeve. A second conductor wire is provided that has at least a third loop. The third loop is positioned between the second flexible insulating sleeve and the first insulating sleeve. The first and second conductor wires are spiraled together so that the third loop is positioned between the first and second loops.

In accordance with another aspect of the present invention, a cardiac lead is provided that includes a first connector and a second connector coupled to a branch assembly. A first flexible insulating sleeve is coupled to the branch assembly. A second flexible insulating sleeve is coupled to the branch assembly and has a portion positioned inside the first flexible insulating sleeve. A first coiled conductor wire is provided that has at least a first loop and a second loop. The first and second loops are positioned around the second flexible insulating sleeve within the branch assembly. A second conductor wire is provided that has a third loop. The first and second conductor wires are spiraled together so that the third loop is positioned between the first and second loops.

BRIEF DESCRIPTION OF THE DRAWINGS

The foregoing and other advantages of the invention will become apparent upon reading the following detailed description and upon reference to the drawings in which:

FIG. 8 is a cross-sectional view of FIG. 6 taken at section 8—8 in accordance with the present invention;

FIG. 9 is a cross-sectional view of one of the filars of a conductor wire of the lead shown in FIGS. 6 and 7 in accordance with the present invention;

DETAILED DESCRIPTION OF SPECIFIC EMBODIMENTS

Background Art

Figure 1:
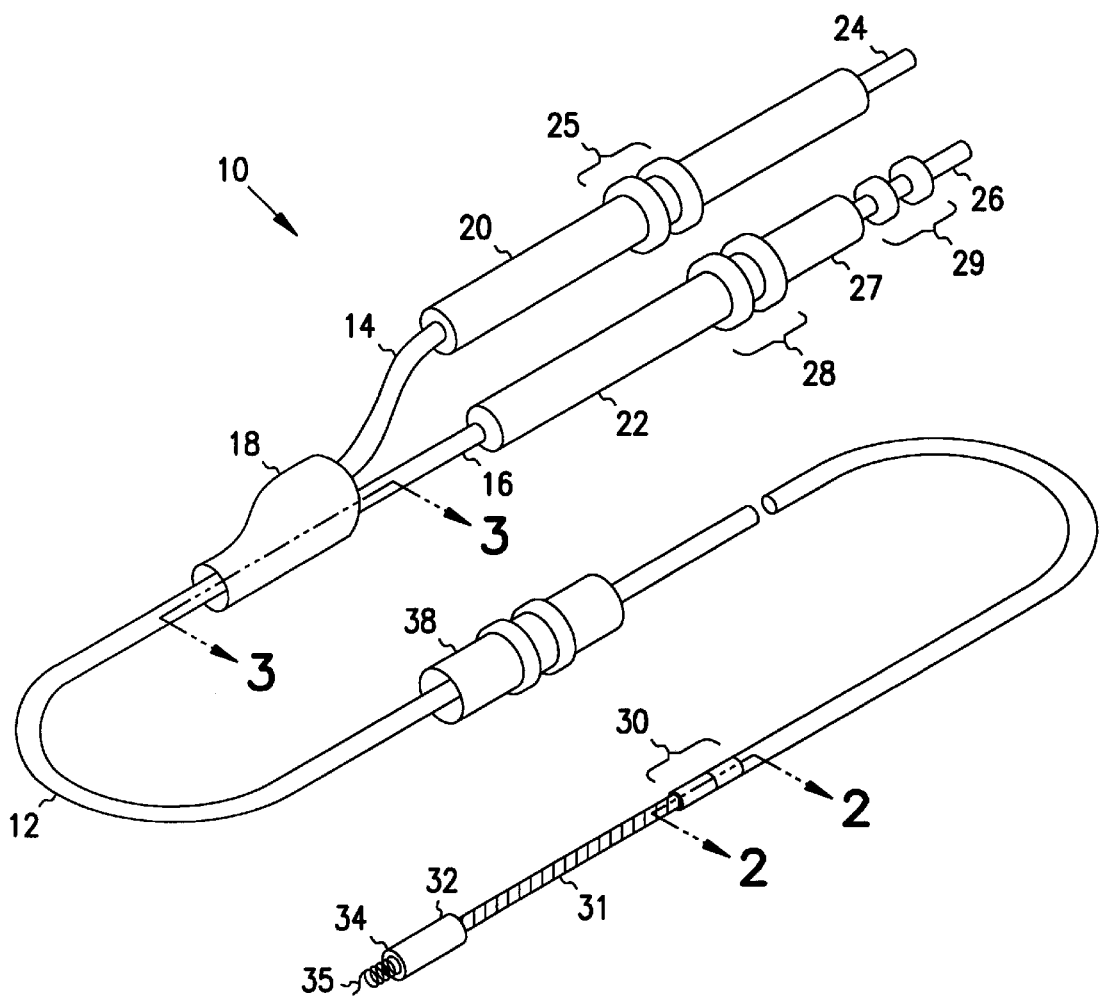
FIG. 1 is a pictorial view of a conventional cardiac stimulator lead.
Figure 2:
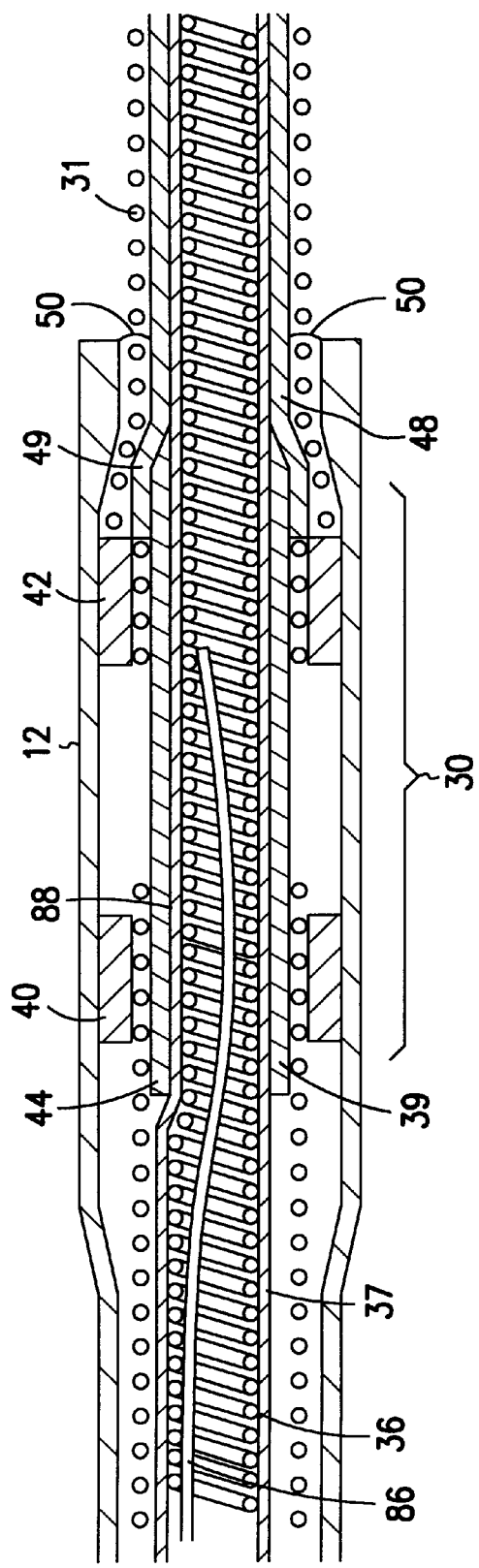
FIG. 2 is a cross-sectional view of FIG. 1 taken at section 2—2.

Turning now to the drawings, and in particular to FIGS. 1 and 2 there is shown an exemplary conventional pacing/defibrillator lead 10 (hereinafter "lead 10"). The lead 10 is provided with a flexible tubular insulating sleeve 12 that divides proximally into segments 14 and 16 at a branch 18. The segment 14 terminates proximally in a connector 20 and the segment 16 terminates proximally in another connector 22. The connectors 20 and 22 are designed to be inserted into a cardiac pacemaker can (not shown). The connector 20 terminates proximally in a pin 24. The pin 24 is connected to a conductor wire positioned inside the segment 14 and the lead sleeve 12 as described more fully below. A set of O-rings 25 is molded to the exterior of the connector 20 to retard the intrusion of body fluids into the pacemaker can. The connector 22 similarly terminates in a connector pin 26. However, the pin 26 is hollow to enable insertion of a stylet inside the lead 10 during implantation. The connector pin 26 is connected to a conductor wire that is positioned in the segment and stretches to the branch 18 as described more fully below. An annular contact 27 is fitted to the connector 22. Pairs of O-rings 28 and 29 are molded to the exterior of the connector 22 to provide a seal against body fluids entering the pacemaker.

The distal end of the insulating sleeve 12 encloses a crimp assembly 30. A defibrillator or shock coil 31 projects distally from the crimp assembly 30, terminating inside a tip sleeve 32. A tip electrode 34 projects slightly from the tip sleeve 32 and is provided with a corkscrew 35 for securing the lead 10 to myocardial tissue. The tip electrode 34 is connected to a conductor wire 36 that extends through the length of the lead 10, terminating at and connecting with the pin 26. The conductor wire 36 is jacketed by an insulating sleeve 37 that is secured distally to tip electrode 34 by a biocompatible medical grade adhesive and proximally over the connector pin 26 in a like manner. A suture sleeve 38 is slipped over the sleeve 12.

The detailed structure of the crimp assembly 30 may be understood by referring now to FIG. 2, which is a cross-sectional view of FIG. 1 taken at section 2—2. The crimp assembly 30 includes an inner crimp sleeve 39 that is positioned inside the insulating sleeve 12. Two outer crimp sleeves 40 and 42 are crimped around the inner crimp sleeve 39. The outer crimp sleeve 40 secures the distal end of a conductor wire 44 to the inner crimp sleeve 39. Similarly, the outer crimp sleeve 42 secures the proximal end of the shock coil 31 to the inner crimp sleeve 39. The inner crimp sleeve 39 is typically composed of a conducting material, such as titanium, that establishes an electrical pathway between the distal end of the conducting wire 44 and the proximal end of the shock coil 31. Another conductor wire 36 passes through the inner crimp sleeve 39 and is connected proximally to the connector pin 26 of the connector 22 shown in FIG. 1, and distally to the tip electrode 34 shown in FIG. 1. The shock coil 31 is disposed around a shock coil sleeve 48. One end 49 of the shock coil sleeve 48 is slipped over the distal end of the inner crimp sleeve 39. The other end is secured to the proximal end of the tip electrode 34 shown in FIG. 1.

The insulating sleeve 12 is slipped around the exterior of the inner crimp sleeve 39 and of the outer crimp sleeves 40 and 42, and secured with medical adhesive. The small gap between the inner diameter of the insulating sleeve 12 and the outer diameter of the shock coil sleeve 48 is sealed with a biocompatible adhesive 50. The conductor wire 44 is individually insulated, save the portion thereof positioned between the outer crimp sleeve 40 and the inner crimp sleeve 39 so that electrical isolation is maintained between the conductor wire 44 and the conductor wire 36 throughout the length of the insulating sleeve 12.

Figure 3:
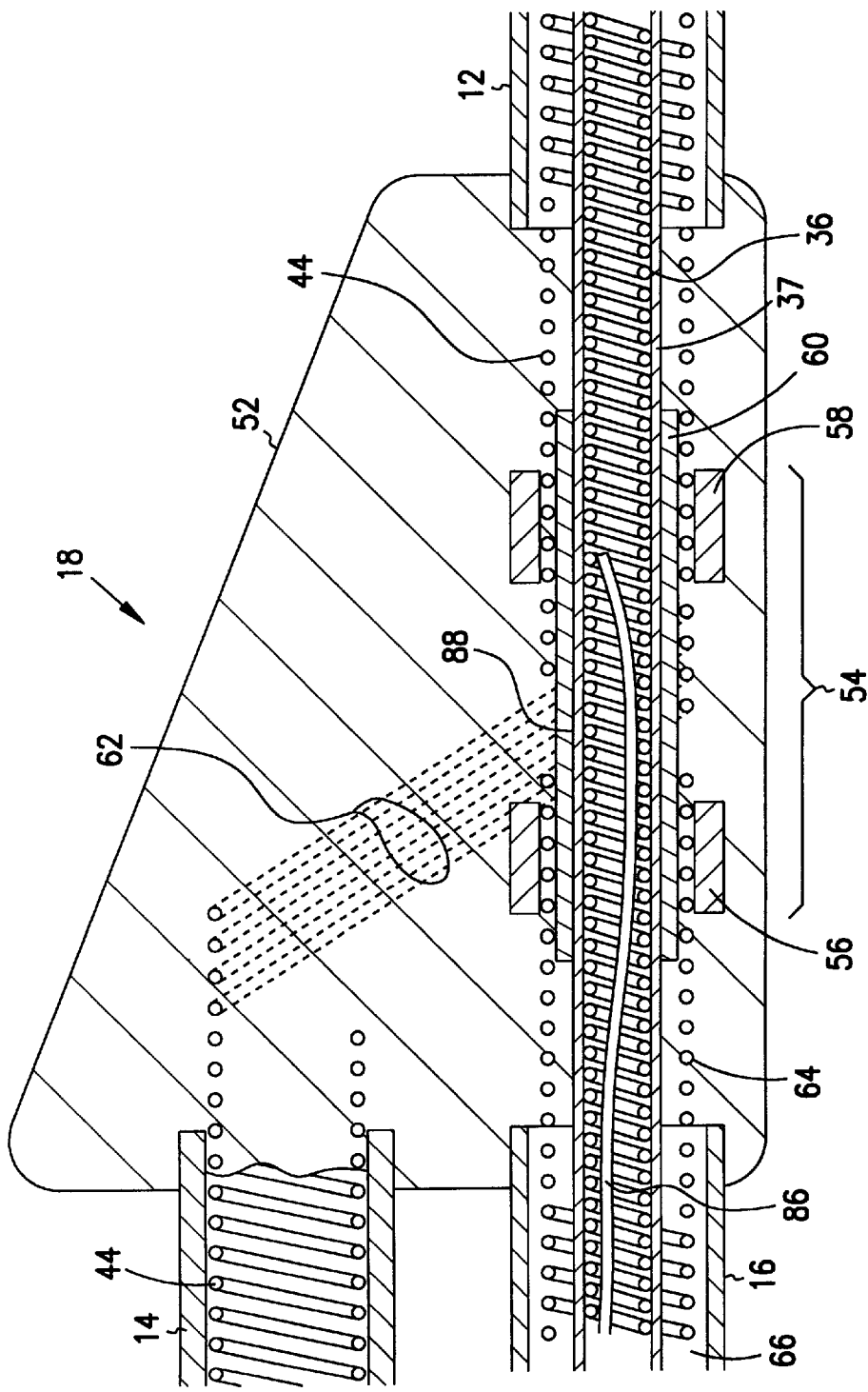
FIG. 3 is a cross-sectional view of FIG. 1 taken at section 3—3.

The detailed structure of the branch 18 may be understood by referring now to FIG. 3, which is a cross sectional view of FIG. 1 taken at section 3—3. The branch 18 includes a branch body 52 that is slipped over and glued around the segment 14, the segment 16 and the insulating sleeve 12 as shown. A crimp assembly 54 is positioned inside the branch body 52 and is structurally identical to the crimp assembly 30 depicted in FIG. 2. Accordingly, the crimp assembly 54 includes outer crimp sleeves 56 and 58 positioned around an inner crimp sleeve 60. The conductor wire 44 is crimped to the inner crimp sleeve 56 by the outer crimp sleeve 58. Proximal to the outer crimp sleeve 58, the conductor wire 44 is uncoiled and routed through the branch body 52 and into the segment 14. The uncoiled filars 62 of the conductor wire 40 are shown in phantom. The distal end of a conductor wire 64 is crimped to the inner crimp sleeve 60 by the outer crimp sleeve 56. The conductor wire 64 is connected proximally to the annular electrode 27 of the connector 22 shown in FIG. 1. Note that the conductor wire 64 and the conductor wire 44 are electrically connected via the conducting inner crimp sleeve 60. The conductor wire 36 passes through the branch body 52 and the inner crimp sleeve 60 and into a tubular sleeve 66 that is positioned inside the segment 16 and extends proximally past the proximal end of the annular electrode 27.

Figure 4:
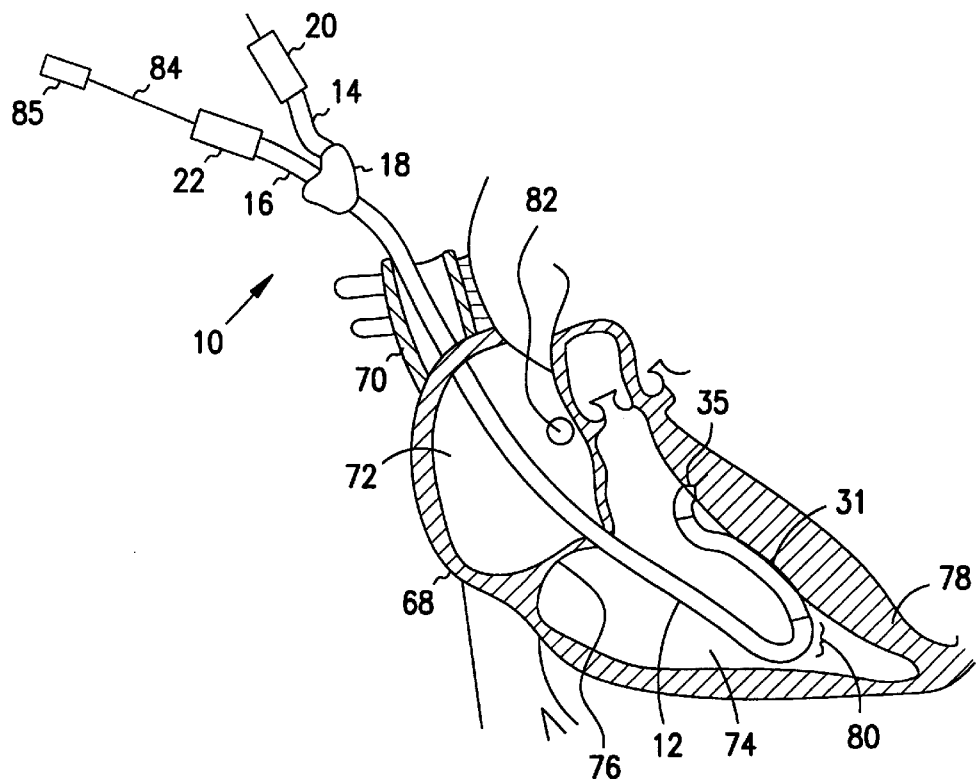
FIG. 4 is a quarter-sectional anterior view of a human heart depicting a typical implantation of the lead shown in FIGS. 1–3.
Figure 5:
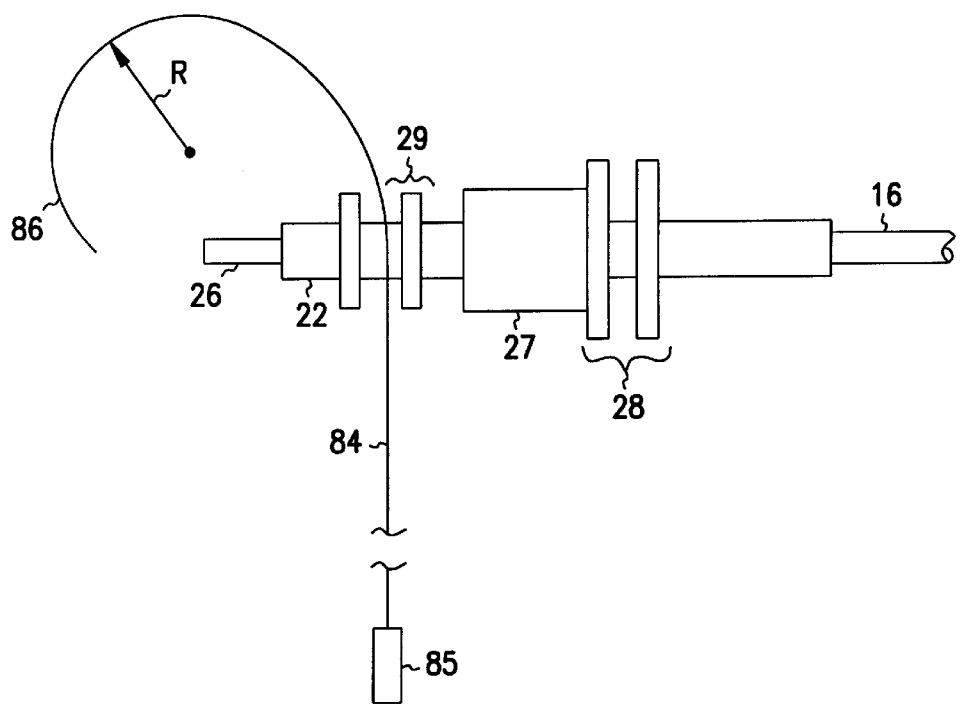
FIG. 5 is a side view of the proximal end of the lead of FIG. 1 depicting insertion of a curved stylet.

An illustrative implantation of the lead 10 may be understood by referring now to FIGS. 4 and 5. FIG. 4 is a quarter-sectional anterior view of a human heart 68. The lead sleeve 12 is introduced into the superior cava 70, and advanced through the right atrium 72 into the right ventricle 74 via the tricuspid valve 76. The corkscrew 35 of the lead 10 is secured superiorly to the interventricular septum 78 and a sufficient portion of the lead sleeve 12 is advanced into the right ventricle 74 so that the shock coil 31 is brought into physical engagement with the interventricular septum 78. In order to establish the requisite engagement with the superior interventricular septum 78, a significant bend 80 must be introduced into the lead 10. Bends in the lead 10, such as the bend 80, are common in implantation procedures involving deviated pathways, such as the pathway depicted in FIG. 4, as well as pathways leading to fixation to the right hand side of the right atrium 68 or pathways involving entry into the coronary sinus 82.

The lead 10 is spatially manipulated by means of a flexible stylet 84 that is inserted into the connector pin 26 of the connector 22 and advanced inside the lead 10 to the tip assembly 32. The stylet 84 is of such length that it is shown broken. A small cylindrical handle 85 is fitted to the stylet 84 to aid the physician in applying thrust to the stylet 84, particularly when a majority of the length of the stylet 84 is already inserted into the lead 10. In order to establish the tight bend 80 in the lead 10, the distal end 86 of the stylet 84 is plastically deformed by hand into a highly curved shape prior to insertion into the pin 26 as shown in FIG. 5. The bending action establishes a relatively small radius of the curvature r for the distal end 86.

The tight bend of the distal end 86 combined with the internal structure of the lead 10 can create difficulties for the physician at the time of implantation. Referring again to FIGS. 2 and 3, as the distal end 86 of the stylet 84 is advanced through the connector 22, the segment 16, and into the branch assembly 18, the generally tubular structure of the connector 22 and the inner sleeve 66 will tend to temporarily and partially straighten the distal end 86. However, the distal end 86 will retain a significant curved portion 88 as shown in FIG. 3. As this highly curved portion 88 passes through the inner crimp sleeve 60, significant rubbing and frictional resistance to longitudinal movement will result. Since the inner crimp sleeve 60 is composed of a relatively rigid material, it cannot temporarily deform to more easily permit the curved portion 88 to pass therethrough.

The resistance to longitudinal movement of the distal end 86 of the stylet 84 through the crimp assembly 54 is normally overcome by applying additional thrust to the portion of the stylet 84 projecting from the connector pin 26 without undue effort. However, the passage of the distal end 86 through the crimp assembly 30 is more problematic. As shown in FIG. 2, as the curved portion 88 of the distal end 86 passes through the crimp assembly 30, the aforementioned rubbing action occurs. The resistance to longitudinal movement of the stylet 84 is now compounded by friction between the stylet 84 and the internal structures of the sleeve 10 proximal to the crimp assembly 30. At this point, the stylet 84 behaves much like an unstable column under compressive load. As thrust is applied to the handle 85 of the stylet 84, and transmitted through the entire length of the extremely thin stylet 84, the stylet 84 will have a tendency to buckle and permanently deform at one or more places between the handle 85 and the highly curved portion 88. These new bends in the stylet 84 can make the behavior of the stylet 84 and the movement of the lead 10 thereby somewhat unpredictable for the physician.

Preferred Embodiment

Figure 6:
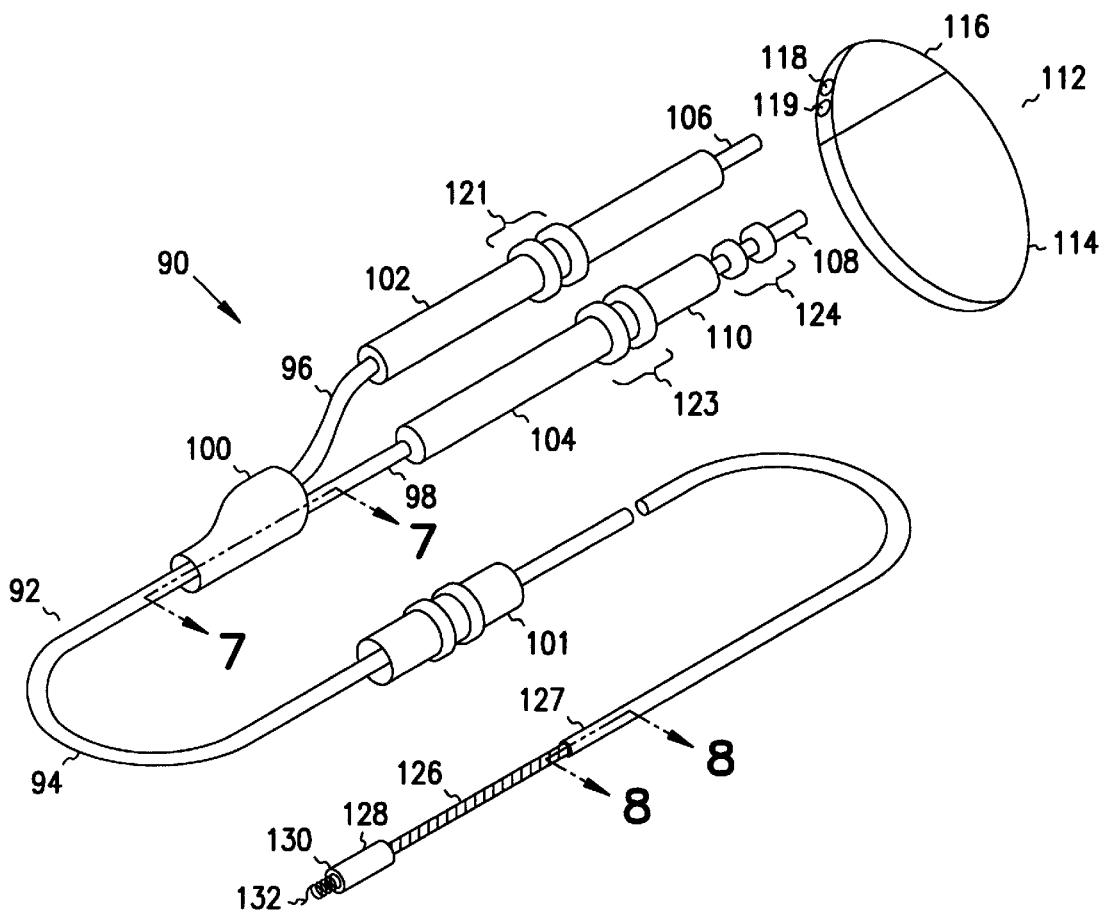
FIG. 6 is pictorial view of an exemplary embodiment of a cardiac lead and a cardiac stimulator in accordance with the present invention.
Figure 7:
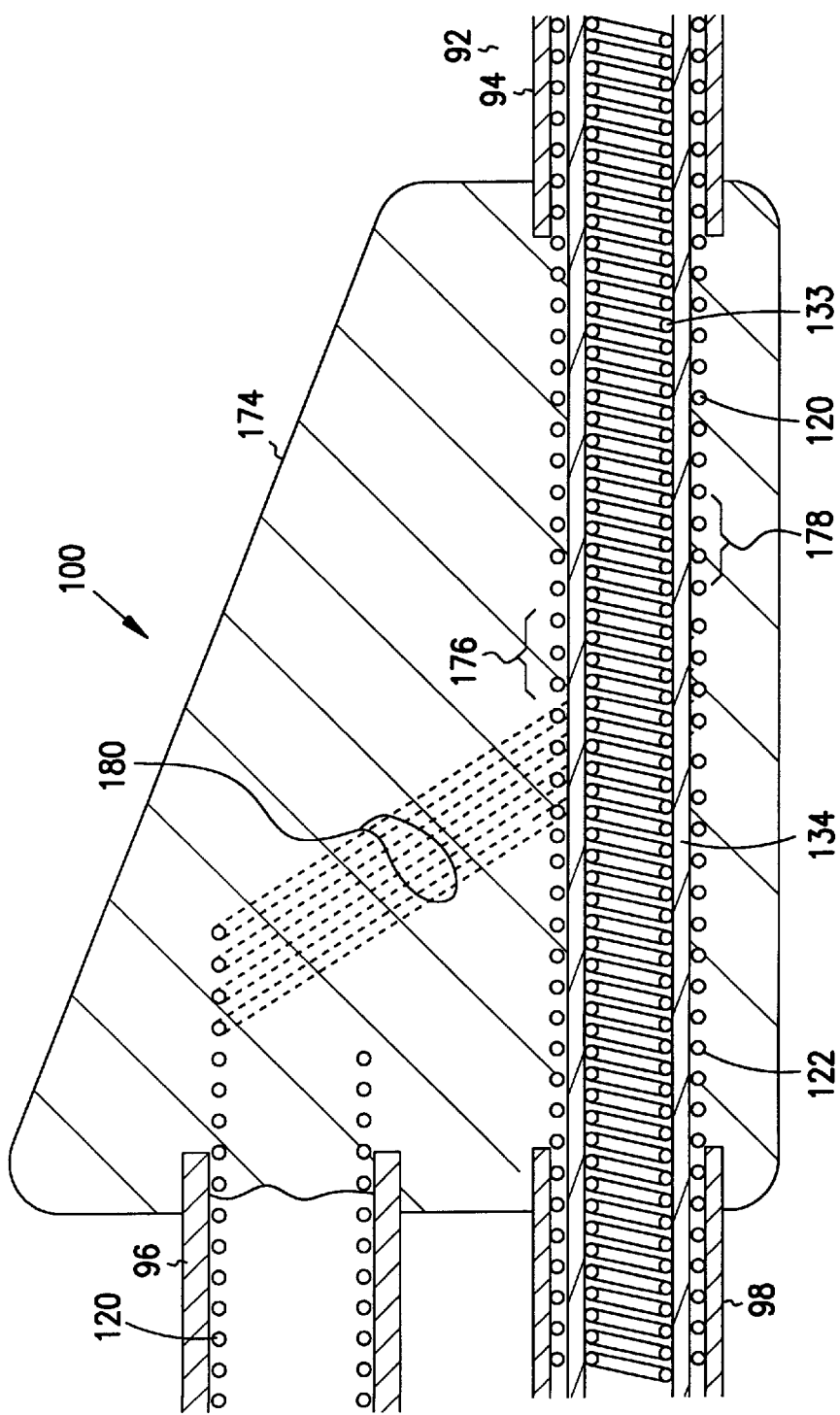
FIG. 7 is a cross-sectional view of FIG. 6 taken at section 7—7 in accordance with the present invention.

An exemplary embodiment of a cardiac stimulator lead 90 in accordance with the present invention may be understood by referring now to FIGS. 6, 7 and 8. This invention eliminates the need for crimp sleeves, described above, thereby improving the flexibility of the lead and the ease of inserting a stylet. FIGS. 7 and 8 are sectional views of FIG. 6 taken, respectively, at sections 7—7 and 8—8. For clarity of illustration, certain components of the lead 90 are shown in full in FIG. 8. The cardiac stimulator lead 90 includes a lead body 92 that has a tubular insulating sleeve 94 which bifurcates proximally into two segments 96 and 98 at a branch assembly 100. The length of the lead body 92 is such that it is shown broken. A suture sleeve 101 is slipped over and used to secure the lead body 92 at a preselected point in the patient's body. The segment 96 terminates in a connector 102 and the segment 98 terminates in a connector 104. The connector 102 is provided with a connector pin 106 and the connector 104 is provided with a connector pin 108 and an annular contact 110. The connectors 102 and 104 are designed to be connected to a cardiac stimulator 112, which consists of a can 114 and a header assembly 116 coupled to the can 114. The header assembly 116 includes ports 118 and 119 into which the connectors 102 and 104 are inserted respectively. The connectors 102 and 104 are shown highly exaggerated in size relative to the remainder of the lead 90 for clarity of illustration. The cardiac stimulator 112 may be a pacemaker, a cardioverter/defibrillator, a sensing instrument, or a combination of these functionalities.

The pin 106 is connected via by crimping, welding or the like to a conductor wire 120 that passes through the segment 96 and the branch assembly 100 and extends into the lead sleeve 94 as described more fully below. The conductor wire 120 is preferably coiled and comprises a plurality of adjacent loops. The conductor 120 may be comprised of one or more filars, each filar lying adjacent the others. A set of O-rings 121 is molded to the exterior of the connector 102 to retard the intrusion of body fluids into the cardiac stimulator header 116. The pin 108 is hollow to enable insertion of a stylet inside the lead 90 during implantation. The connector pin 108 is connected via by crimping, welding or the like to a conductor wire 122 that passes through the segment 98 and terminates in the branch assembly 100 as described more fully below. The conductor wire 122 is preferably coiled and comprises a plurality of adjacent loops. The conductor may be comprised of one or more filars, each filar lying adjacent the others. Pairs of O-rings 123 and 124 are molded to the exterior of the connector 104 to retard body fluid intrusion. The exterior of the connectors 102 and 104 may be composed of a biocompatible electrically insulating material, such as silicone, polyurethane or the like, and the pins 106 and 108 may be fabricated from stainless steel, titanium or the like.

The detailed structure of the lead body 92 may be understood by referring to FIG. 8. For clarity of illustration only the insulating sleeve 94 is actually shown in section in FIG. 8 while the remaining the components are shown in full. A defibrillator or shock coil 126 projects distally from the distal end 127 of the insulating sleeve 94, terminating inside a tip sleeve 128. The proximal end of the shock coil 126 is intertwined proximally with the distal end of the conductor wire 120 at the region designated 129. The conductor wire 120 is connected proximally to the connector pin 106 shown in FIG. 6 by crimping, welding or the like. The shock coil 126 delivers defibrillating pulses from the cardiac stimulator 112 to myocardial tissue. A tip electrode 130 projects slightly from the tip sleeve 128 and is provided with a corkscrew 132. The corkscrew 132 is used to secure the tip electrode 130 to myocardial tissue, and may be augmented and/or substituted with one or more radially spaced tines or other type of fixation mechanism. The tip electrode 130 supplies pacing pulses from the cardiac stimulator 112 to myocardial tissue and transmits sensing signals from myocardial tissue back to the cardiac stimulator 112. An electrical pathway between the tip electrode 130 and the connector pin 108 is established by a conductor wire 133 that is connected distally to the tip electrode 130 by biocompatible medical grade adhesive, crimping, welding or the like, and extends through the length of the lead 90, terminating at and connecting to the pin 108 by like methods.

Both the conductor wire 120 and the shock coil 126 are positioned around an inner sleeve 134 that is coupled distally to the tip electrode 130 inside the tip sleeve 128 by biocompatible medical grade adhesive, crimping or like methods, and proximally to the connector 104 shown in FIG. 6 by like methods. Note that a portion of the inner sleeve 134 is cut away to reveal the conductor wire 133 positioned therein. The conductor wire 133 is disposed inside the inner sleeve 134. The inner sleeve 134 is designed to take most if not all of any tensile load applied to the lead body 92, and to electrically insulate the conductor wire 133 from the conductor wires 120 and the 126.

The insulating sleeve 94 is designed to provide a flexible protective shroud for the conductor wire 120 and the portion of the shock coil 126 connected to the conductor wire 120. The segments 96 and 98 of the sleeve 94 provide structurally robust physical connections between the connectors 102 and 104 and the branch assembly 100. Accordingly, the insulating sleeve 94 is advantageously a flexible tubular structure composed of a biocompatible material, such as silicone, polyurethane or the like. In an exemplary embodiment, the insulating sleeve 94 is composed of silicone. The inner sleeve 134 and the tip sleeve 128 may be similarly composed. While flexibility is a desired characteristic for both the insulating sleeve 94 and the inner sleeve 134, it is not necessarily a prerequisite for the tip sleeve 128.

The tip electrode 130 may be fabricated from a variety of biocompatible conducting materials, such as iridium oxide coated titanium, MP35N alloy, stainless steel, platinum-iridium alloy consisting of approximately 90% platinum and 10% iridium, or some other biocompatible conducting metal, or a semiconductor material, such as silicon, or other semiconductor material.

The detailed structure of the conductor wire 120 may be understood by referring now also to FIG. 9, which is a cross sectional view of one of the filars of the wire 120. The conductor wire 120 is a four-filar coiled wire, with each filar consisting of a conductor 135A individually coated with an insulating jacket 135B. The conductor 135A may include a plurality of filaments 136 as shown or a single filament. The conductor 135A may be composed of a variety of biocompatible conducting materials, such as MP35N alloy, stainless steel, titanium or like materials. In an exemplary embodiment, the conductor 135A is composed of drawn-brazed strands ("DBS") or filaments 136 of stainless steel. The insulating coating 135B may be composed of a variety of biocompatible insulating materials, such as ETFE (fluoropolymer resin) or like materials. The skilled artisan will appreciate that another form of conductor wire may be used, such as, for example, a single filar insulated or uninsulated wire.

The shock coil 126 is a three-filar coiled wire. The filars may be composed of a variety of biocompatible conducting materials, such as MP35N alloy, stainless steel, titanium or like materials. In an exemplary embodiment, the filars are composed of iridium oxide coated titanium. Iridium oxide provides excellent resistance to corrosion caused by body fluids. As with the conductor wire 120, the skilled artisan will appreciate that the shock coil 126 may take on another form, such as, for example, a six filar wire.

Referring again to FIG. 8, the inner sleeve 134 provides the structural member necessary to take tensile loads applied to the lead body 92. Accordingly, the connection between the conductor wire 120 and the shock coil 126 may be established without crimping or an assembly like the conventional crimp assembly 30 shown in FIG. 2. In this regard, the conductor wire 120 may be reliably secured to the shock coil 126 by intertwining at least one of the loops 137 of the conductor wire 120 and at least one of the loops 138 of the shock coil 126 as shown in FIG. 8. The intertwining of the loops 137 of the four-filar conductor wire 120 and the loops 138 of the tri-filar shock coil 126 is accomplished by plastically deforming a portion of the conductor wire 120 prior to assembly. The nominal or undeformed pitch $P_0$ between adjacent loops is shown in FIG. 8. The goal of the plastic deformation process is expand the pitch of at least adjacent loops, in this case the loops 137 and 139, from the undeformed pitch $P_0$ to the expanded pitch $P_1$. The expanded pitch $P_1$ enables the coil 138 of the shock coil 126 to, in essence, be screwed together with the loops 137 and 139 of the conductor wire 120 so that the loop 138 is positioned between the loops 137 and 139.

Figure 10:
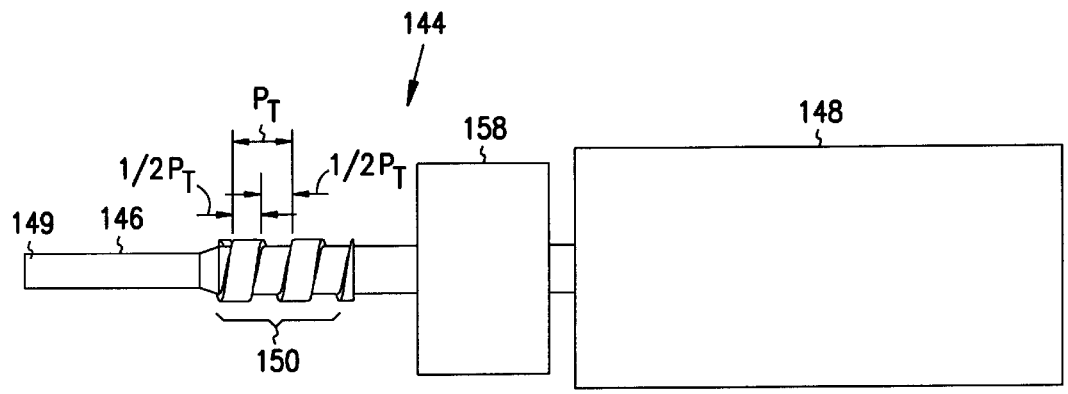
FIG. 10 is a side view of an exemplary embodiment of a wire coil spreader in accordance with the present invention.
Figure 11:
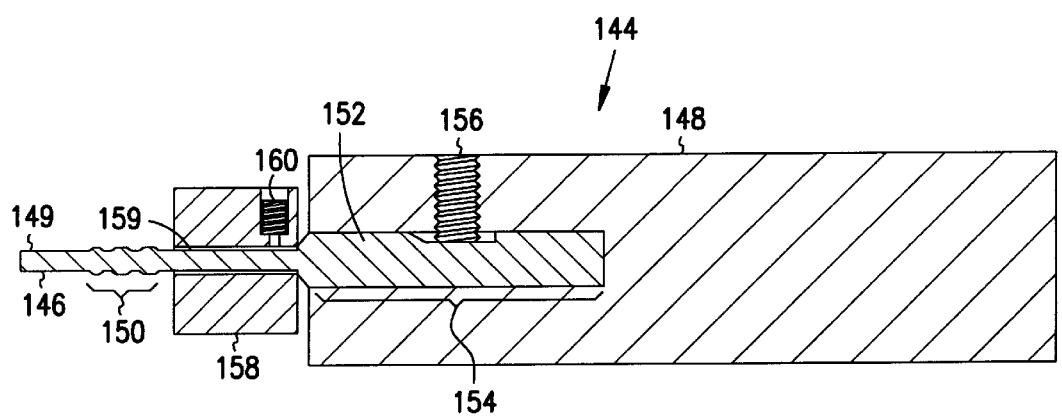
FIG. 11 is a cross-sectional view of the coil spreader shown in FIG. 10 in accordance with the present invention.

The deformation of the conductor wire 120 to achieve the desired pitch $P_1$ of the sets of loops 137 and 139 may be accomplished using a coil spreader 144, an exemplary embodiment of which is depicted in FIGS. 10 and 11. FIG. 10 is a side view of the coil spreader 144 and FIG. 11 is a sectional view of the coil spreader 144. The coil spreader 144 includes a mandrel 146 that is secured to a handle 148. The distal end 150 of the mandrel 146 is provided with a set of external threads or grooves 150 that are cut or otherwise formed in the mandrel 146 with a pitch direction, that is, left handed or right handed, that matches the pitch direction of the conductor wire 120. The grooves 150 are also formed with pitch $P_T$, and are helical and square. The width $W_R$ of each root is equal to the diameter of the filars multiplied by the number of filars in the coil. The width of each crest $W_C$ is equal to $P_T-W_R$. The pitch $P_T$ is related to the ultimately desired pitch $P_1$ of loops of the conductor wire 120 according to the expression:

$$P_T - X = P_1$$

where X is the anticipated elastic recovery of the conductor wire 120 following removal from the mandrel 146.

The distal end 149 of the mandrel 146 is provided with an outer diameter that is just slightly less than the inner diameter of the conductor wire 120 to enable the conductor wire 120 to be readily slipped over the distal end 149. The proximal end 152 of the mandrel 146 is positioned in a bore 154 in the handle 148 and secured thereto by a set screw 156. A collar 158 is positioned over the mandrel via in internal bore 159 and is provided with a set screw 160 that is designed to engage the conductor wire 120 as described below.

Figure 12:
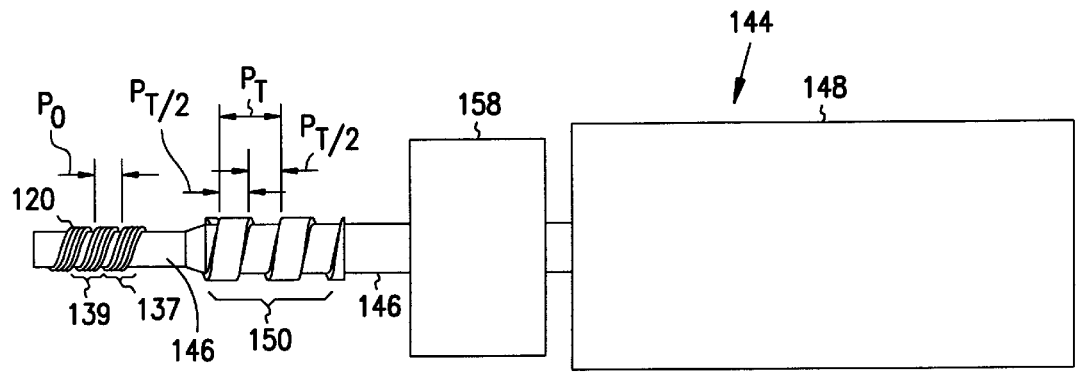
FIG. 12 is a side view like FIG. 10 showing a conductor wire positioned thereon prior to coil spreading in accordance with the present invention.
Figure 13:
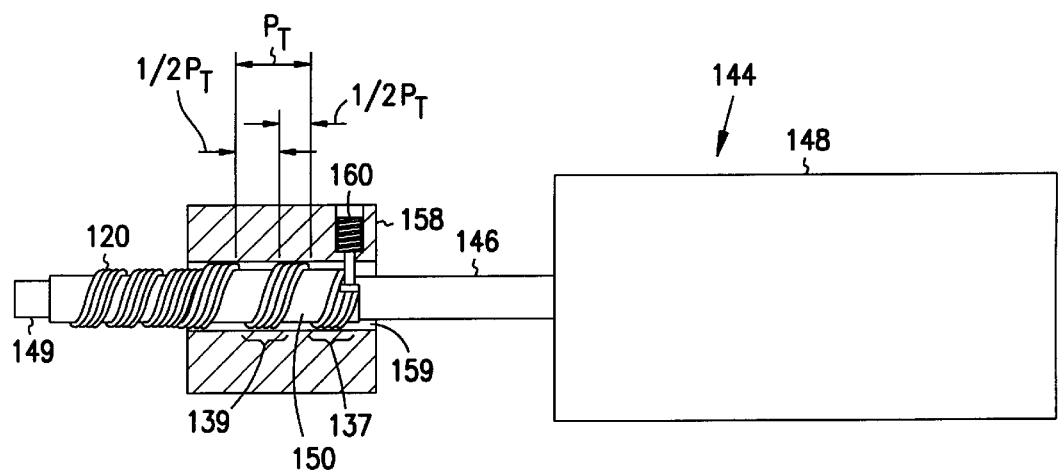
FIG. 13 is a view like FIG. 12 depicting the wire after coil spreading in accordance with the present invention.

The coil spreading operation may be understood by referring now to FIGS. 12 and 13, which are side views like FIG. 10 prior to and during the engagement of the threads 150 by the conductor wire 120. Referring initially to FIG. 12, the conductor wire 120 is slipped over the mandrel 146. At this point, the conductor wire 120 has a nominal pitch $P_0$ defined generally by the spacing between the first filar of loop and a point on the first filar the next adjacent loop of the coil. As noted above, the threads 150 are formed with a pitch $P_T$ and are helical and square so that the width of the root of each thread is $W_R$ and the width of each crest is $P_T-W_R$. Referring now to FIG. 13, the collar 158 is slipped over the threads 150 and the set screw 160 is tightened until it bottoms out on the mandrel 146. The collar 158 prevents the coils 137 and 139 from slipping out of the grooves 150 during advancement through the threads 150. The conductor wire 120 is advanced until the distal end of the conductor wire 120 engages the threads 150. At this point, the conductor wire 120 is rotated, according to the pitch direction of the threads 150, in this case counterclockwise. As the conductor wire 120 is rotated, the adjacent loops 137 and 139 are spread apart by the threads 150 and plastically deformed to assume a new pitch. The conductor wire 120 may be rotated until the end thereof abuts the side of the set screw 160. To remove the wire 120 from the grooves 150, the collar 158 is rotated to unscrew the coils 137 and 139 from the threads 150. As the collar 158 is rotated, the set screw 160 pushes against the end of the loop 137 to unscrew the wire 120 from the mandrel 146. If necessary, the set screw 160 may be loosened slightly to enable free rotation of the collar 158. The plastic deformation of the loops 137 and 139 is almost instantaneous. Thus, the conductor wire 120 may be spiraled off the mandrel 146 without delay.

The spreading of the loops 137 and 139 will not result in complete plastic deformation. Instead, the loops 137 and 139 will undergo some recovery of magnitude X upon removal from the mandrel 146. Accordingly, the threads 150 are cut such that $P_T-X$ is approximately equal to the desired final pitch $P_1$ of the coils.

Figure 14:
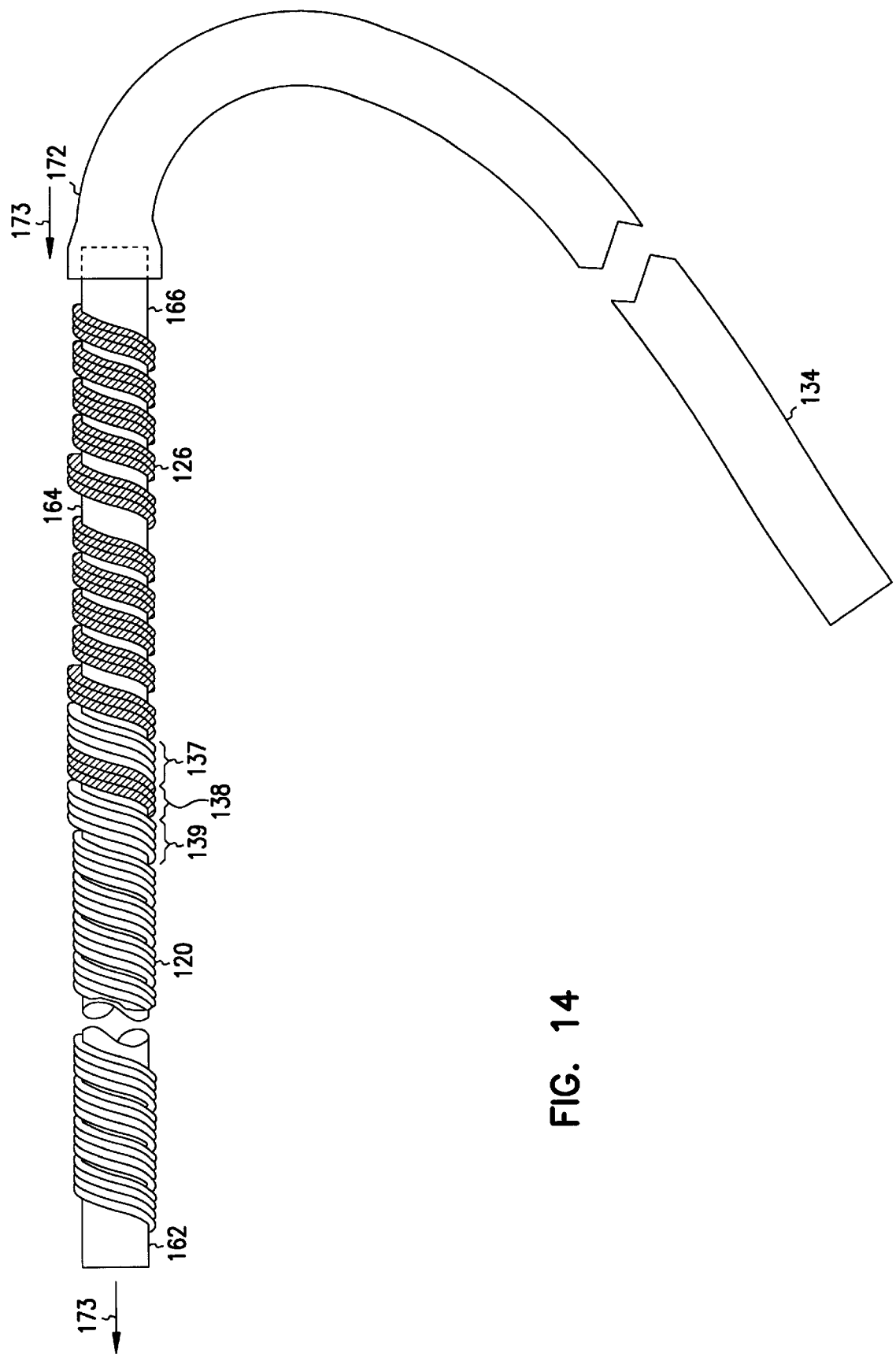
FIGS. 14 and 15 are side views of two conductor wires of the lead of FIG. 6 depicting the process of intertwining of the two wires.
Figure 15:
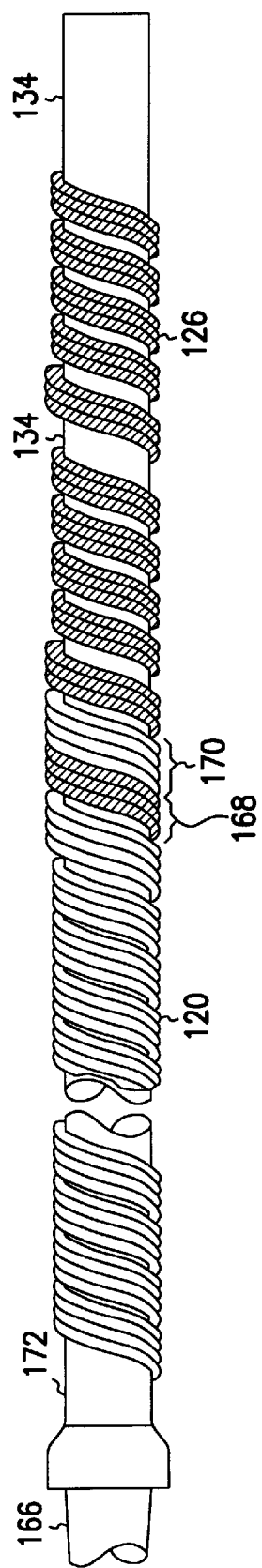

The assembly of the conductor wire 120 with the shock coil 126 following the coil spreading procedure may be understood by referring now to FIGS. 14 and 15, which are, respectively, side views of the conductor wire 120 and the shock coil 126 during and after assembly. Referring initially to FIG. 14, the conductor wire 120 is slipped over the left end 162 of a mandrel 164 and the shock coil 126 is slipped over the right end 166 of the mandrel 164 and moved into contact with the conductor wire 120. The conductor wire 120 and shock coil 126 are then intertwined by rotating either the conductor wire 120 or the shock coil 126 or both so that the loops 137 and 139 of the wire 120 and the loop 138 of the shock coil 126 screw together as shown. The mandrel 164 will be removed and replaced with the inner sleeve 134. This transition may be eased by first slipping the proximal end 172 of the inner sleeve 134 over the distal end 166 of the mandrel 164. Then, by pulling the mandrel in the direction of the arrows 173, the inner sleeve 134 will automatically slide inside the shock coil 126 and the conductor wire 120. Note that the inner sleeve 134 is of such length that it is shown broken and that the outer diameter of the proximal end 172 thereof is shown exaggerated in size relative to the distal end 166 of the mandrel 164. FIG. 15 shows the inner sleeve 134 after being pulled inside the shock coil 126 and the conductor wire 138. At this point, the distal end 166 of the mandrel may be disconnected from the proximal end 172 of the inner sleeve 134. Electrical contact between the conductor wire 120 and the shock coil 126 takes place through physical contact of adjacent filars where the two coils are threaded together. This contact may be enhanced by encasing this area in a conductive adhesive such as gold or silver impregnated epoxy, silicon or an elastomeric polymer.

The detailed structure of the branch assembly 100 may be understood by referring again to FIG. 7. The branch assembly 100 includes a branch body 174 that is slipped over and glued around the segments 96 and 98 and the insulating sleeve 94 with a biocompatible medical grade adhesive. The branch body 174 is designed to provide a biocompatible, electrically insulating and readily moldable junction structure. Accordingly, the branch body 174 may be composed of a variety of biocompatible moldable insulating materials, such as silicone, polyurethane, or the like.

The wires 120 and 122 are connected to enable bipolar pacing. Pacing pulses generated by the cardiac stimulator 112 are transmitted to the tip electrode 130 (see FIGS. 6 and 8) via the connector pin 108 and the conductor wire 133. Return pulses from myocardial tissue during pacing are routed back to the cardiac stimulator 1 12 through the annular contact 110 (see FIG. 6). The pathway for return pulses from myocardial tissue back to the annular contact 110 is through the shock coil 126, the conductor wire 120, and finally the conductor wire 122. The conductor wire 122 may take on a variety of configurations, such as single filar, multi-filar or the like and may be composed of the same types of materials used to fabricate the conductor wire 120. In an exemplary embodiment, the wire 122 is an uncoated, coiled three-filar wire composed of drawn brazed strands of stainless steel MP35N steel.

The engagement between the conductor wire 122 and the conductor wire 120 inside the branch body 174 is substantially identical to the configuration depicted in FIG. 8. The loops of the conductor wire 120 are spread as described above in conjunction with FIGS. 12 and 13 so that the loops of the tri-filar conductor wire 122 may be intertwined therewith at 176 and 178. The conductor wire 120 is unfurled proximal to the coil of the wire 122 at 176 and positioned in longitudinal alignment with the segment 96. The unfurling establishes arcuate sections 180 of the filars in the branch body 174 that are shown in phantom. Electrical contact between the two conductor wires 120, 122 takes place through physical contact of adjacent filars where the two coiled wires are threaded together. This contact is also enhanced by encasing this area in a conductive matrix such as the silver-polymer matrix mentioned above. The branch assembly is completed by gluing the branch body 174 around the segments 96, 98 and the insulating sleeve 94, as described above.

The lead body of the present invention incorporating intertwined conductor wires 120 and 126 spiraled around the flexible inner sleeve 134 (see FIG. 8) essentially eliminates rigid tubing through which the implanting physician might otherwise have to traverse a stylet during implantation of a conventional lead. For the implanting physician, the flexibility of the entire length of the lead body 92 means that the lead body 92 will more easily conform to the curvature of the stylet. The result is less resistance to passage of the stylet, less potential for buckling of the stylet, and a better tactile response for the physician.

The foregoing illustrated embodiments included the union of a shock coil 126 and a conductor wire 120 (see FIGS. 6, 7 and 8). However, the skilled artisan will appreciate the combination of the inner sleeve 134 and the intertwining of coils may be used to join a myriad of different types of conductor wires, either in a branched lead as shown, or in a lead incorporating a single insulating lead sleeve. The loops of one of the wires may be spread as shown or the loops of both may be spread prior to intertwining as desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead, comprising:
   a connector for coupling to a cardiac stimulator;
   a first flexible insulating sleeve coupled to the connector;
   a second flexible insulating sleeve coupled to the connector and having a portion positioned inside the first flexible insulating sleeve;
   a first conductor wire having a coiled portion with at least a first loop and a second loop, the first and second loops being positioned between the first flexible insulating sleeve and the portion of the second flexible insulating sleeve positioned inside the first flexible insulating sleeve; and
   a second conductor wire having a coiled portion with at least a third loop, the third loop being positioned between the first flexible insulating sleeve and the portion of the second flexible insulating sleeve positioned inside the first flexible insulating sleeve, and between the first and second loops the first and second conductor wires being spiraled together so that electrical contact is formed between said first and second conductor wires at a location wherein the third loop is positioned between the first and second loop.

2. The cardiac lead of claim 1, wherein the second insulating sleeve has a second portion positioned outside said first insulating sleeve and the second conductor wire has a plurality of loops positioned adjacent said second portion of said second insulating sleeve.

3. The cardiac lead of claim 2, wherein the second conductor wire has three filars.

4. The cardiac lead of claim 1, wherein the first and second insulating sleeves are composed of silicone.

5. The cardiac lead of claim 1, wherein the first loop and the second loop are located on a distal end of the first conductor wire, and wherein the third loop is located on a proximal end of the second conductor wire.

6. A cardiac lead, comprising:
   a branch assembly;
   a first connector and a second connector coupled to the branch assembly;
   a first flexible insulating sleeve coupled to the branch assembly;
   a second flexible insulating sleeve coupled to the branch assembly and having a portion positioned inside the first flexible insulating sleeve;
   a first conductor wire having a coiled portion with at least a first loop and a second loop, the first and second loops being positioned around the second flexible insulating sleeve within the branch assembly; and
   a second conductor wire having a coiled portion with at least a third loop, the first and second conductor wires being spiraled together so that the third loop is positioned between the first and second loops.

7. The cardiac lead of claim 6, wherein the branch assembly comprises molded silicone.

8. The cardiac lead of claim 6, wherein the first conductor wire comprises a conductor coated with an insulating jacket.

9. The cardiac lead of claim 8, wherein of the first conductor wire comprises a plurality of conducting filaments.

10. The cardiac lead of claim 6 wherein the first, second and third loops are further electrically connected by an electrically conductive adhesive.

11. A cardiac lead, comprising:
    a connector for coupling to a cardiac stimulator;
    a first flexible insulating sleeve coupled to the connector;
    a second flexible insulating sleeve coupled to the connector and having a portion positioned inside the first flexible insulating sleeve;
    a first conductor wire comprising a conductor partially coated with an insulating jacket, the first conductor wire having a coiled portion with at least a first loop and a second loop, the first and second loops being positioned between the first flexible insulating sleeve and the portion of the second flexible insulating sleeve positioned inside the first flexible insulating sleeve; and
    a second conductor wire at least partially spiraled together with the first conductor wire, the second conductor wire having a coiled portion with at least a third loop, the third loop being positioned between the first flexible insulating sleeve and the portion of the second flexible insulating sleeve positioned inside the first flexible insulating sleeve, the third loop positioned between the first loop and the second loop so that an electrical contact is formed between said first and second conductor wires.

12. The cardiac lead of claim 11, wherein the conductor of the first conductor wire comprises a plurality of conducting filaments.

13. The cardiac lead of claim 11, wherein the second flexible insulating sleeve has a second portion positioned outside said first insulating sleeve and the second conductor wire has a plurality of loops positioned adjacent said second portion of said second insulating sleeve.

14. The cardiac lead of claim 13, wherein the plurality of loops are coated with iridium oxide.

15. The cardiac lead of claim 11, wherein the second conductor wire has three filars.

16. The cardiac lead of claim 11, wherein the first and second insulating sleeves are composed of silicone.

17. The cardiac lead of claim 11 wherein said first, second and third loops are further electrically connected by an electrically conductive adhesive.

18. A cardiac lead, comprising:
    a connector for coupling to a cardiac stimulator;
    a first flexible insulating sleeve coupled to the connector;
    a second flexible insulating sleeve coupled to the connector and having a first portion positioned inside the first flexible insulating sleeve and a second portion positioned outside the first flexible insulating sleeve;
    a first conductor wire having a coiled portion with at least a first loop and a second loop, the first and second loops being positioned between the first flexible insulating sleeve and the first portion of the second flexible insulating sleeve; and a second conductor wire at least partially spiraled together with the first conductor wire, the second conductor wire having a coiled portion with at least a third loop, the third loop being positioned between the first flexible insulating sleeve and the first portion of the second flexible insulating sleeve, the third loop positioned between the first loop and the second loop so that an electrical contact is formed between said first and second conductor wires;

wherein, the second conductor wire has a plurality of loops positioned adjacent the second portion of the second insulating sleeve, and wherein the plurality of loops are coated with iridium oxide.

19. The cardiac lead of claim 18, wherein the second conductor wire has three filars.

20. The cardiac lead of claim 18, wherein the first and second insulating sleeves are composed of silicone.

21. A cardiac lead, comprising:

a connector for coupling to a cardiac stimulator;

a first flexible insulating sleeve coupled to the connector;

a second flexible insulating sleeve coupled to the connector and having a portion positioned inside the first flexible insulating sleeve;

a first conductor wire having a coiled portion with at least a first loop and a second loop, the first and second loops being positioned between the first flexible insulating sleeve and the portion of the second flexible insulating sleeve positioned inside the first flexible insulating sleeve; and a second conductor wire at least partially spiraled together with the first conductor wire, the second conductor wire having a coiled portion with at least a third loop, the third loop being positioned between the first flexible insulating sleeve and the portion of the second flexible insulating sleeve positioned inside the first flexible insulating sleeve, the third loop positioned between the first loop and the second loop so that an electrical contact is formed between said first and second conductor wires;

wherein said first, second and third loops are further electrically connected by an electrically conductive adhesive.

22. The cardiac lead of claim 21, wherein the second conductor wire has three filars.

23. The cardiac lead of claim 21, wherein the first and second insulating sleeves are composed of silicone.

24. The cardiac lead of claim 21, wherein the second insulating sleeve has a second portion positioned outside said first insulating sleeve and the second conductor wire has a plurality of loops positioned adjacent said second portion of said second insulating sleeve.

* * * * *